US010105323B2

(12) United States Patent
Messerschmid et al.

(10) Patent No.: US 10,105,323 B2
(45) Date of Patent: *Oct. 23, 2018

(54) PHARMACEUTICAL DOSAGE FORM FOR IMMEDIATE RELEASE OF AN INDOLINONE DERIVATIVE

(71) Applicant: Boehringer Ingelheim International GmbH, Ingelheim am Rhein (DE)

(72) Inventors: Roman Messerschmid, Biberach an der Riss (DE); Peter Lach, Ulm (DE); Torsten Sokoliess, Neu-Ulm (DE); Peter Stopfer, Warthausen (DE); Dirk Trommeshauser, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/590,487

(22) Filed: May 9, 2017

(65) Prior Publication Data

US 2017/0239191 A1 Aug. 24, 2017

Related U.S. Application Data

(63) Continuation of application No. 14/848,563, filed on Sep. 9, 2015, now abandoned, which is a continuation of application No. 14/176,478, filed on Feb. 10, 2014, now abandoned, which is a continuation of application No. 13/790,334, filed on Mar. 8, 2013, now abandoned, which is a continuation of application No. 12/995,893, filed as application No. PCT/EP2009/056895 on Jun. 4, 2009, now abandoned.

(30) Foreign Application Priority Data

Jun. 6, 2008 (EP) .................... 08157750

(51) Int. Cl.
| | |
|---|---|
| *A61K 9/50* | (2006.01) |
| *A61K 31/4045* | (2006.01) |
| *A61K 31/4439* | (2006.01) |
| *C07D 209/34* | (2006.01) |
| *A61K 31/496* | (2006.01) |
| *A61K 9/48* | (2006.01) |
| *A61K 9/00* | (2006.01) |
| *A61K 47/26* | (2006.01) |
| *A61K 9/10* | (2006.01) |
| *A61K 9/20* | (2006.01) |
| *A61K 31/403* | (2006.01) |
| *A61K 31/661* | (2006.01) |
| *C07D 401/06* | (2006.01) |
| *C07D 401/14* | (2006.01) |
| *C07D 403/06* | (2006.01) |
| *C07D 403/14* | (2006.01) |
| *C07F 9/572* | (2006.01) |
| *C07F 9/6558* | (2006.01) |

(52) U.S. Cl.
CPC .......... *A61K 9/5078* (2013.01); *A61K 9/0095* (2013.01); *A61K 9/10* (2013.01); *A61K 9/2027* (2013.01); *A61K 9/2054* (2013.01); *A61K 9/4858* (2013.01); *A61K 31/403* (2013.01); *A61K 31/4045* (2013.01); *A61K 31/4439* (2013.01); *A61K 31/496* (2013.01); *A61K 31/661* (2013.01); *A61K 47/26* (2013.01); *C07D 209/34* (2013.01); *C07D 401/06* (2013.01); *C07D 401/14* (2013.01); *C07D 403/06* (2013.01); *C07D 403/14* (2013.01); *C07F 9/572* (2013.01); *C07F 9/6558* (2013.01)

(58) Field of Classification Search
CPC .... A61K 9/50; A61K 31/403; A61K 31/4045; A61K 31/4439; C07D 209/34
See application file for complete search history.

(56) References Cited

U.S. PATENT DOCUMENTS

| | | | |
|---|---|---|---|
| 2,870,062 | A | 1/1959 | Stanley et al. |
| 4,780,316 | A | 10/1988 | Brox |
| 5,817,323 | A | 10/1998 | Hutchinson et al. |
| 6,169,106 | B1 | 1/2001 | Heckel et al. |
| 6,319,918 | B1 | 11/2001 | Heckel et al. |
| 6,762,180 | B1 | 7/2004 | Roth et al. |
| 6,858,641 | B2 | 2/2005 | Roth et al. |
| 7,119,093 | B2 | 10/2006 | Roth et al. |
| 7,176,221 | B2 | 2/2007 | Gierer |
| 7,989,474 | B2 | 8/2011 | Roth et al. |
| 8,067,617 | B2 | 11/2011 | Merten et al. |
| 8,304,541 | B2 | 11/2012 | Merten et al. |
| 8,802,384 | B2 | 8/2014 | Arao et al. |
| 2005/0043233 | A1 | 2/2005 | Stefanic et al. |

(Continued)

FOREIGN PATENT DOCUMENTS

| | | |
|---|---|---|
| JP | 561058537 | 3/1986 |
| JP | 071381151 | 5/1995 |

(Continued)

OTHER PUBLICATIONS

Abstract in English for WO 2014/194795, publication date Dec. 11, 2014.

(Continued)

*Primary Examiner* — Shirley V Gembeh
(74) *Attorney, Agent, or Firm* — Paula K. Wittmayer; David L. Kershner

(57) ABSTRACT

The present invention relates to a pharmaceutical dosage form delivering an immediate release profile containing the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

10 Claims, 10 Drawing Sheets

(56) References Cited

U.S. PATENT DOCUMENTS

Figure 1:
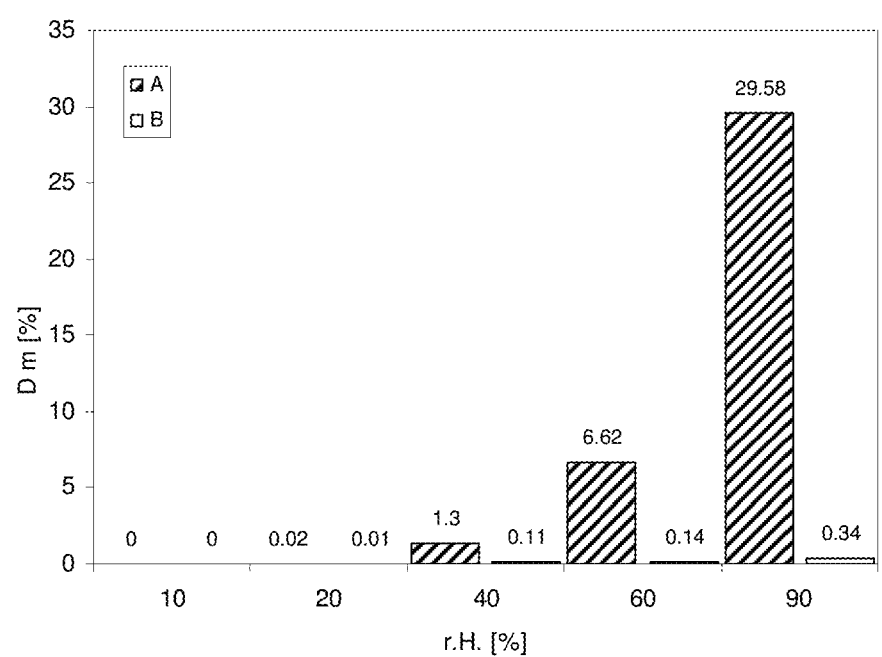

| | | |
|---|---|---|
| 2006/0058311 A1 | 3/2006 | Munzert et al. |
| 2006/0142373 A1 | 6/2006 | Park et al. |
| 2006/0293260 A1 | 12/2006 | Albright |
| 2009/0306101 A1 | 12/2009 | Solca et al. |
| 2010/0233705 A1 | 9/2010 | Arao et al. |
| 2011/0178099 A1 | 7/2011 | Stefanic et al. |
| 2011/0301177 A1 | 12/2011 | Messerschmid et al. |
| 2012/0142703 A1 | 6/2012 | Van Ryn et al. |
| 2012/0157472 A1 | 6/2012 | Larsen et al. |
| 2015/0265610 A1 | 9/2015 | Stefanic et al. |
| 2016/0136133 A1 | 5/2016 | Park et al. |
| 2016/0143906 A1 | 5/2016 | Gaschler-Markefski et al. |
| 2016/0250218 A1 | 9/2016 | Stefanic et al. |

FOREIGN PATENT DOCUMENTS

| | | |
|---|---|---|
| JP | 2002291419 A | 10/2002 |
| JP | 2005074303 A | 3/2005 |
| WO | 2009500123 | 1/1995 |
| WO | 1999052869 A1 | 10/1999 |
| WO | 1999062882 A1 | 12/1999 |
| WO | 2000073297 A1 | 12/2000 |
| WO | 0108507 A1 | 2/2001 |
| WO | 2001027080 A2 | 4/2001 |
| WO | 2002081445 A1 | 10/2002 |
| WO | 2004013099 A1 | 2/2004 |
| WO | 2004096224 A2 | 11/2004 |
| WO | 2006018182 A1 | 2/2006 |
| WO | 2006067165 A2 | 6/2006 |
| WO | 2006127487 A1 | 11/2006 |
| WO | 2007054551 A1 | 5/2007 |
| WO | 2009071523 A1 | 6/2009 |
| WO | 2009147218 A1 | 12/2009 |
| WO | 2010081817 A1 | 7/2010 |
| WO | 2010103058 A1 | 9/2010 |
| WO | 2010130757 A1 | 11/2010 |
| WO | 2014194795 A1 | 12/2014 |

OTHER PUBLICATIONS

Hilberg, F. et al., "Efficacy of BIBF 1120, a potent triple angiokinase inhibitor, in models of human non-small cell lung cancer is augmented by chemotherapy." Journal of Thoracic Oncology, 2007, vol. 2, No. 8, Suppl. 4, p. S380.

International Search Report for PCT/EP2009/056895 dated Sep. 14, 2009.

Pan, W., "Industrial Pharmacy." Higher Education Press, 2006, pp. 322-323.

U.S. Appl. No. 15/204,277, filed Jul. 7, 2016, Inventor: Roman Messerschmid.

Jianming, Associated Press of Beijing Medical Univ, 1995, p. 252-254.

PHARMACEUTICAL DOSAGE FORM FOR IMMEDIATE RELEASE OF AN INDOLINONE DERIVATIVE

The present invention relates to a pharmaceutical dosage form delivering an immediate release profile containing the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

BACKGROUND TO THE INVENTION

The rate and extent to which the active ingredient or active moiety is absorbed from a pharmaceutical dosage form and becomes available at the site of action is defined as bioavailability (Chen, M. L. et al. , Bioavailability and bioequivalence: an FDA regulatory overview, Pharm. Res. 2001, 18, 1645-1648).

However, it is rarely feasible to measure the drug at the site of action. Therefore, bioavailability is assessed based on drug concentrations in the general circulation. The systemic exposure is determined by measuring the blood or plasma concentrations of the active drug at numerous time points following the drug administration and calculation of the area under the concentration-time curve (AUC). Blood/plasma drug concentration time profiles are affected by the dynamics of dissolution, solubility, absorption, metabolism, distribution, and elimination.

Drug absorption from a solid dosage form after administration depends on the release of the drug substance from the drug product, the dissolution or solubilization of the drug under physiological conditions, beside its permeability across the gut wall of the gastrointestinal tract. A higher dissolution rate of a formulation generally increases liberation out of the dosage form up to a maximum extent, which is a prerequisite for adequate bioavailability of an ingredient or active moiety. Because of the critical nature of this step, in vitro dissolution may be relevant to the prediction of in vivo plasma concentrations and therefore bioavailability. (Guidance for Industry, Dissolution Testing of Immediate Release Solid Oral Dosage Forms, U.S. Department of Health and Human Services, Food and Drug Administration, Center for Drug Evaluation and Research (CDER), Aug. 1997). An observed in vivo difference in the rate and extent of absorption of a drug depends on the speed of drug dissolution in vivo. (Amidon, G. L. et al., A Theoretical Basis For a Biopharmaceutics Drug Classification: The Correlation of In Vitro Drug Product Dissolution and In Vivo Bioavailability, Pharmaceutical Research, 12: 413-420 (1995)).

Based on this general consideration, in vitro dissolution tests for immediate release solid oral dosage forms, such as tablets and capsules, are used to assess the quality of a drug product. An immediate release product allows the active to dissolve in the gastrointestinal tract, without causing any delay or prolongation of the dissolution or absorption of the drug. Requirements for dissolution testing of immediate release products are focused in the Guidance for Industry (CDER 1997) Dissolution testing for immediate release solid oral dosage forms, (CDER 1997) Immediate release solid oral dosage forms—Scale up and Postapproval Changes, ICH Guidance Q6A, Specifications: Test Procedures and Acceptance Criteria For New Drug Substances And New Drug Products. The most commonly employed dissolution test methods as described in the European Pharmacopeia 6.2 ($6^{th}$ edition) are the basket method (Apparatus 1) and the paddle method (Apparatus 2). The described methods are simple, robust, well standardized, and used worldwide. They are flexible enough to allow dissolution testing for a variety of drug products. Consistent with established regulatory guidance (e.g. European Pharmacopeia 6.2, $6^{th}$ edition), the following parameters influencing the dissolution behaviour may for example be relevant for selecting the appropriate in vitro dissolution test conditions for an immediate release solid oral product: Apparatus, stirring speed, dissolution medium and temperature.

3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate is an innovative substance having valuable pharmacological properties, especially for the treatment of oncological diseases, immunologic diseases or pathological conditions involving an immunologic component, or fibrotic diseases.

The chemical structure of this substance is depicted below as Formula (I).

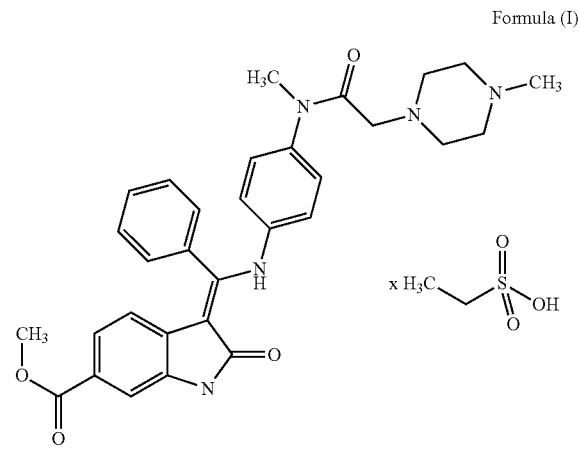

Formula (I)

This substance is described as base in WO 01/27081, as monoethanesulfonate salt form in WO 2004/013099, for its use in the treatment of immunologic diseases or pathological conditions involving an immunologic component in WO 2004/017948, for its use in the treatment of oncological diseases in WO 2004/096224, for its use in the treatment of fibrotic diseases in WO 2006/067165, and as other salt forms in WO 2007/141283.

The aim of the present invention is to obtain for the above drug substance a pharmaceutical dosage form which meets adequate bioavailability requirements for the desired target dosage range and which is further characterized by a specific immediate release profile range providing an appropriate plasma concentration-time profile of the active principle. Such specific release profile characteristic is not known from the prior art for this drug substance.

SUMMARY OF THE INVENTION

A first object of the present invention is a pharmaceutical dosage form of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate which delivers an immediate release profile in which not less than 70% (Q65%) of the active substance is dissolved in 60 minutes in vitro under the following in vitro dissolution conditions according to European Pharmacopeia 6.2: Apparatus 2

(paddle), dissolution medium with 0.1 M HCl (pH 1) and stirring speed of 50 to 150 rpm, at a temperature of 37° C.

A further object of the present invention is the above pharmaceutical dosage form which, under the above conditions, delivers an immediate release profile in which not less than 75% (Q 70%) of the active substance is dissolved in 60 minutes in vitro.

A further object of the present invention is the above pharmaceutical dosage form which, under the above conditions, delivers an immediate release profile in which not less than 85% (Q 80%) of the active substance is dissolved in 60 minutes in vitro, preferably not less than 85% (Q 80%) of the active substance is dissolved in 45 minutes in vitro, most preferably not less than 85% (Q 80%) of the active substance is dissolved in 30 minutes in vitro.

A further object of the present invention is the above pharmaceutical dosage form which, under the above conditions, exhibits comparable in vitro dissolution profiles independent from a dosage strength of 5 to 1000 mg of the active substance, preferably between 25 to 300 mg of the active substance.

A further object of the present invention is a pharmaceutical dosage form of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate which delivers an immediate release profile in which the maximum concentration of the analyte/active substance in plasma at steady state ($C_{max,ss}$) increases in a dose-proportional manner, preferably when the dose range of the active substance is between 50 and 300 mg.

A further object of the present invention is a pharmaceutical dosage form of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate which delivers an immediate release profile in which the dose-normalized maximum concentration of the analyte/active substance in plasma at steady state ($C_{max,ss,norm}$) is similar for different doses, preferably when the dose range of the active substance is between 50 and 300 mg.

A further object of the present invention is a pharmaceutical dosage form of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate which delivers an immediate release profile in which the area under the plasma concentration-time curve of the analyte/active substance in plasma at steady state over a dosing interval τ ($AUC_{\tau,ss}$) increases in a dose-proportional manner, preferably when the dose range of the active substance is between 50 and 300 mg.

A further object of the present invention is a pharmaceutical dosage form of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate which delivers an immediate release profile in which the dose-normalized area under the plasma concentration-time curve of the analyte/active substance in plasma at steady state over a dosing interval τ ($AUC_{96,ss,norm}$) is similar for different doses, preferably when the dose range of the active substance is between 50 and 300 mg.

A further object of the present invention is a pharmaceutical dosage form of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate which delivers an immediate release profile, characterized in that it reaches a maximum plasma concentration in the blood of a human subject within less than between 0.75 and 6 hours, preferably with a median value of 2 hours.

A further object of the present invention is a pharmaceutical dosage form of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate which delivers an immediate release profile, wherein the maximum plasma concentration in the plasma of human subjects is at least within a range of 4 ng/ml and 32 ng/ml, with a geometric mean value of 14 ng/ml, if a dosage form comprising 150 mg (3 times 50 mg) of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate has been administered.

A further object of the present invention is the above pharmaceutical dosage form, wherein it is an orally deliverable dosage form.

A further object of the present invention is the above pharmaceutical dosage form which is in the form of a tablet, capsule, oral solution, elixir, emulsion, pellets, powder or granules.

A further object of the present invention is the above pharmaceutical dosage form which comprises a suspension of the active substance.

A further object of the present invention is the above pharmaceutical dosage form in which the suspension of the active substance is a viscous suspension of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate comprising a carrier and a thickener.

A further object of the present invention is the above pharmaceutical dosage form in which the carrier is a lipid (lipophilic) carrier.

A further object of the present invention is the above pharmaceutical dosage form wherein under the following in vitro dissolution conditions according to European Pharmacopeia 6.2 the lipid suspension is dispersed in small droplets: Apparatus 2 (paddle), dissolution medium with 0.1 M HCl (pH 1) and stirring speed of 50 to 150 rpm, at a temperature of 37° C.

A further object of the present invention is the above pharmaceutical dosage form in the form of a capsule comprising a capsule shell and a capsule formulation, characterized in that the capsule formulation is the above suspension of the active substance.

A further object of the present invention is the above pharmaceutical dosage form in the form of a capsule, characterised in that the capsule shell is fast disintegrating in vitro, which is a prerequisite for fast liberation of the active in vivo as well.

A further object of the present invention is the above pharmaceutical dosage form for use as medicament.

A further object of the present invention is the above pharmaceutical dosage form for use as pharmaceutical composition with an antiproliferative activity.

A further object of the present invention is the above pharmaceutical dosage form for the treatment of a disease or condition selected from oncological diseases, immunologic diseases or pathological conditions involving an immunologic component, and fibrotic diseases.

A further object of the present invention is the use of the above pharmaceutical dosage form for the preparation of a medicament for the treatment of a disease or condition selected from oncological diseases, immunologic diseases or pathological conditions involving an immunologic component, and fibrotic diseases.

A further object of the present invention is a process for the treatment and/or prevention of a disease or condition selected from oncological diseases, immunologic diseases or pathological conditions involving an immunologic component, and fibrotic diseases, characterised in that an effective amount of the above defined pharmaceutical dosage form is administered orally to a patient once or several times daily.

A further object of the present invention is the above pharmaceutical dosage form comprising the active substance in an amount of 0.01 to 90 wt.-%, preferably 0.1 to 50 wt.-% of the composition.

A further object of the present invention is the above pharmaceutical dosage form which comprises dose-range values of between 5 to 1000 mg of the active substance, preferably between 25 to 300 mg of the active substance.

A further object of the present invention is the above pharmaceutical dosage form which is used in a body-weight-independent (BWI) dosing.

A further object of the present invention is the above pharmaceutical dosage form for use in a dosage range of from 0.1 mg to 20 mg of active substance/kg body weight, preferably 0.5 mg to 5 mg active substance/kg body weight.

LEGEND TO THE FIGURES

FIG. 1—Mass gain by moisture sorption (Dm in %) under different relative humidity conditions (r.H. in %) for a soft gelatin capsule (A) and for a lipid suspension formulation (B).

Figure 2:
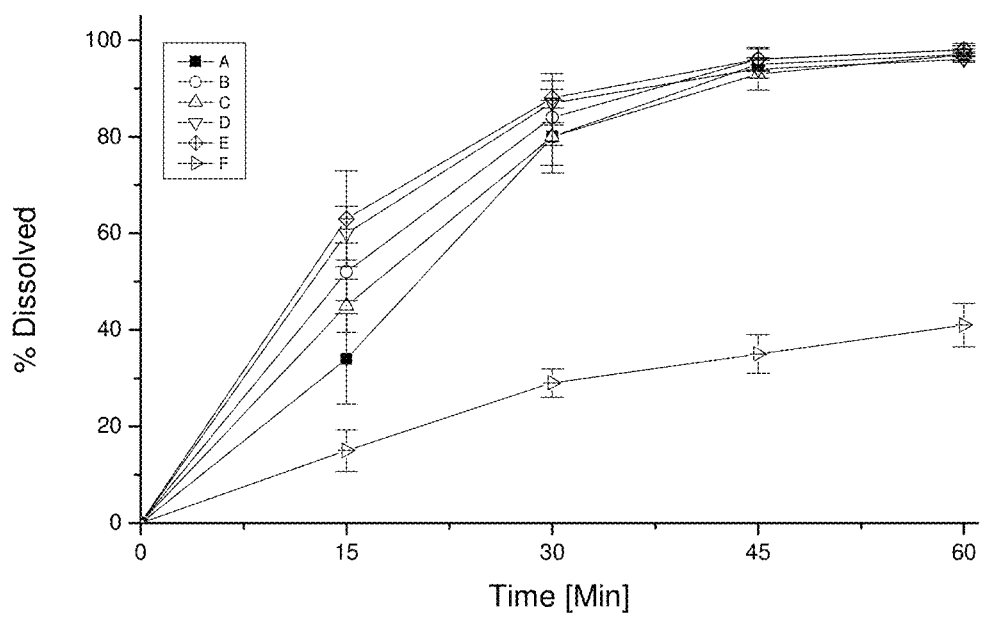

FIG. 2—Effect of the employed lecithin amount in a 150 mg soft gelatin capsule on the in vitro dissolution behaviour. Dissolution tests with Apparatus 2 (paddle), 100 rpm, 900 mL pH 1.0 (0.1 M HCl) dissolution medium, 37° C.: (A) 30% lecithin of preferred amount, (B) 75% lecithin of preferred amount, (C) 90% lecithin of preferred amount, (D) preferred amount of lecithin (equals to 100%), (E) 200% lecithin of preferred amount, (F) 0% lecithin.

Figure 3:
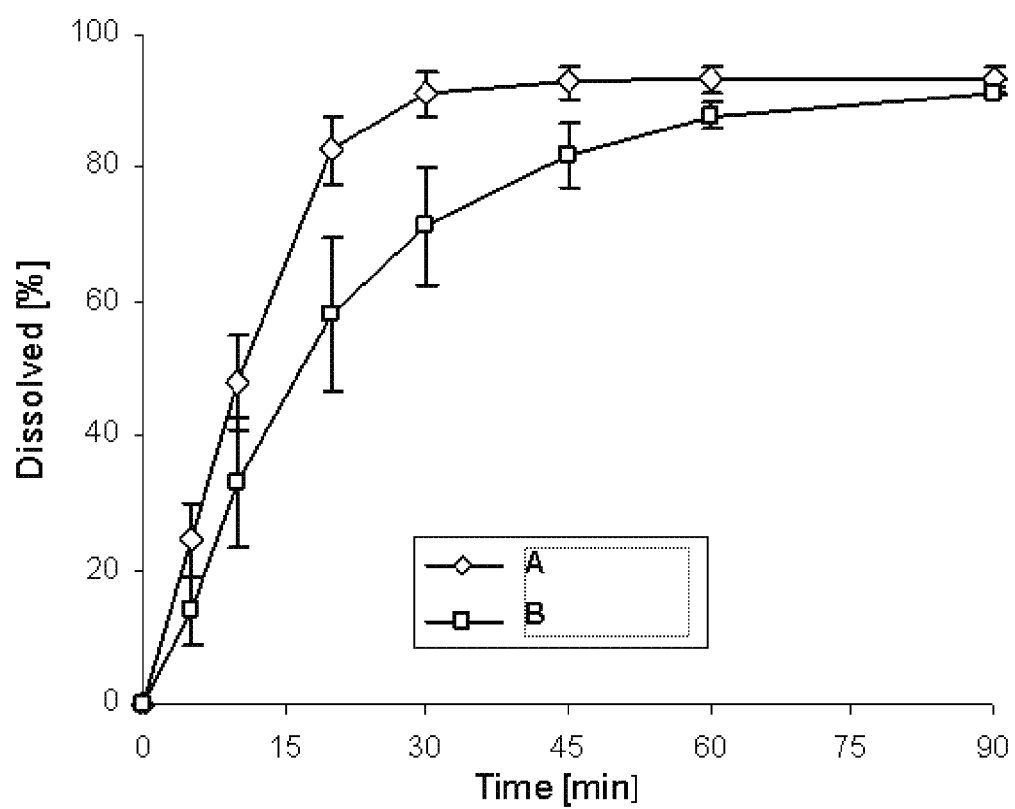

FIG. 3—Effect of the melting range of the hard fat on the in-vitro dissolution behaviour (in % of dissolution) over time (in minutes) of soft gelatin capsules. Dissolution tests with Apparatus 2 (paddle), 100 rpm, 900 mL pH 1.2 dissolution medium, 37° C.: (A) melting range of 33° C.-40° C., (B) melting range of 40° C. - 44 ° C.

Figure 4:
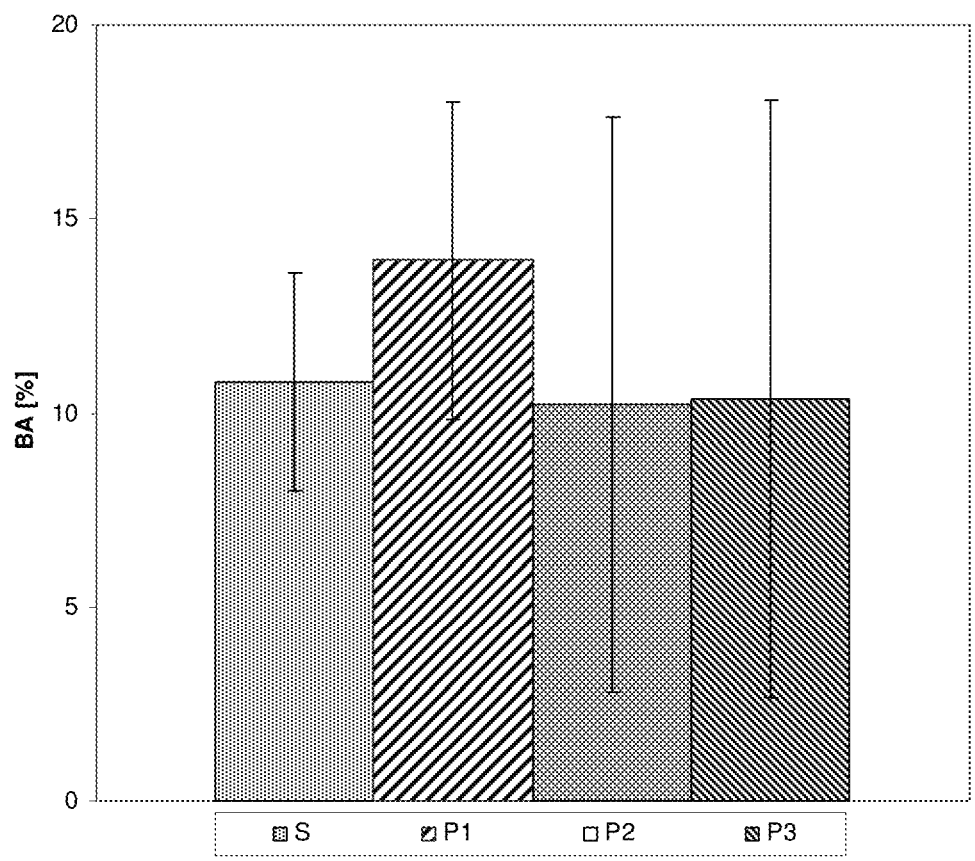

FIG. 4—Comparison of the absolute bioavailability (BA in %) tested in the rat over 24 hours for the aqueous solution (S) versus different carrier systems (P1, P2 and P3) of the active substance—Error bars indicate standard deviations.

Figure 5:
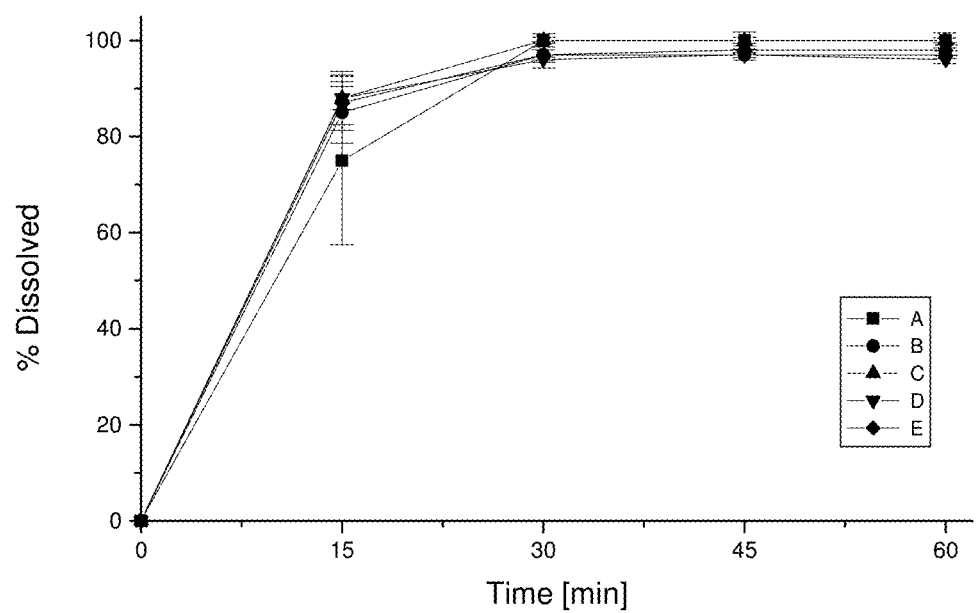

FIG. 5—Influence of the dosage strength in the range 50 mg-150 mg of active substance (compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate) on the in vitro dissolution behaviour of soft gelatin capsules. Dissolution tests with Apparatus 2 (paddle), 100 rpm, 900 mL pH 1.0 (0.1 M HCl) dissolution medium, 37° C.: (A) 50 mg active substance, (B) 75 mg active substance, (C) 100 mg active substance, (D) 125 mg active substance, (E) 150 mg active substance.

Figure 6:
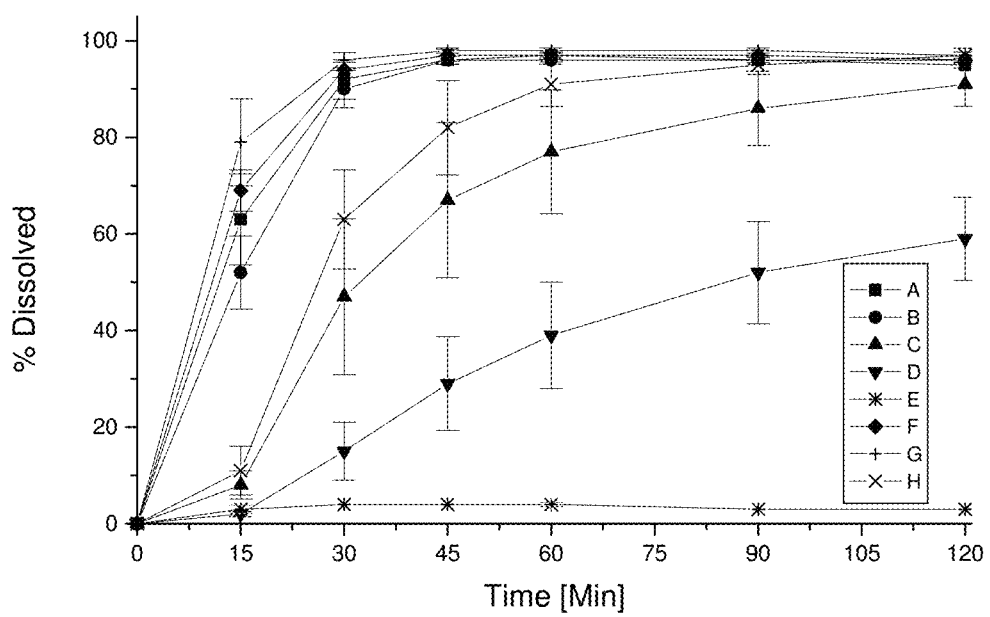

FIG. 6—Influence of the dissolution media pH and the presence of surfactants on the in vitro dissolution behaviour of 150 mg soft gelatin capsules. Dissolution profile comparison of 150 mg soft gelatin capsules in the dissolution media pH 1.0 and pH 3.0, with and without surfactants. Dissolution tests with Apparatus 2 (paddle), 100 rpm, 900 mL dissolution media in the pH range 1.0 to 6.8, 37° C.: (A) pH 1.0, (B) pH 2.0, (C) pH 3.0, (D) pH 4.0, (E) pH 6.8., (F) pH 1.0 and 0.5% Cremophor, (G) pH 1.0 and 0.5% Tween 80, (H) pH 3.0 and 0.5% Tween 80.

Figure 7:
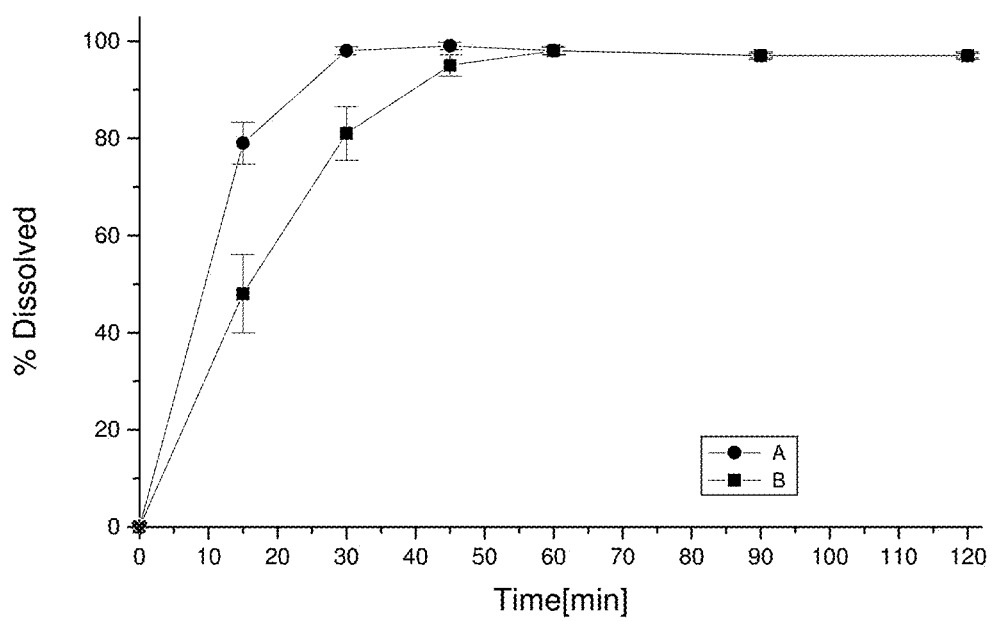
Figure 8:
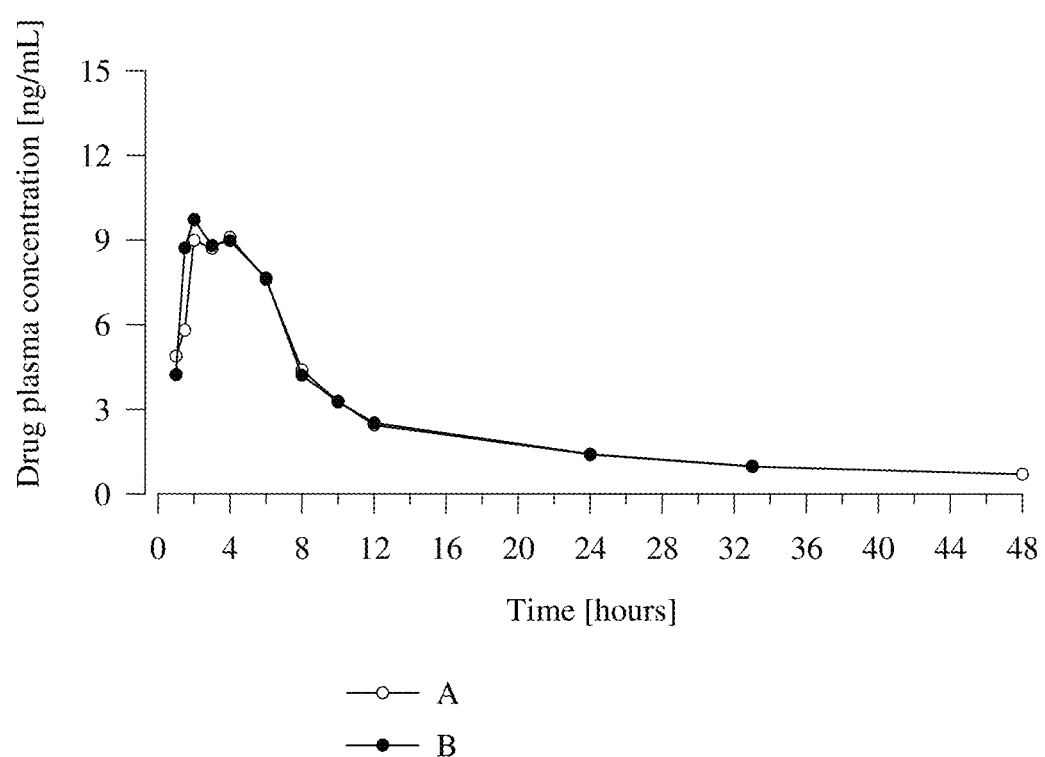

FIG. 7—Dissolution curve of different 50 mg soft gelatin capsule batches used in the study of FIG. 8, showing a fast and a slow in vitro dissolution profile. Dissolution tests with Apparatus 2 (paddle), 100 rpm, 900 mL pH 1.0 (0.1 M HCl) dissolution medium, 37° C.: (A) fast, (B) slow.

FIG. 8—Geometric mean plasma concentration—time profiles of formulations of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate with slower (A, 3×50 mg soft gelatin capsules) and with faster in vitro release (B, 3×50 mg soft gelatin capsules) in a human bioavailability study. The plasma concentration refers to the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone.

Figure 9:
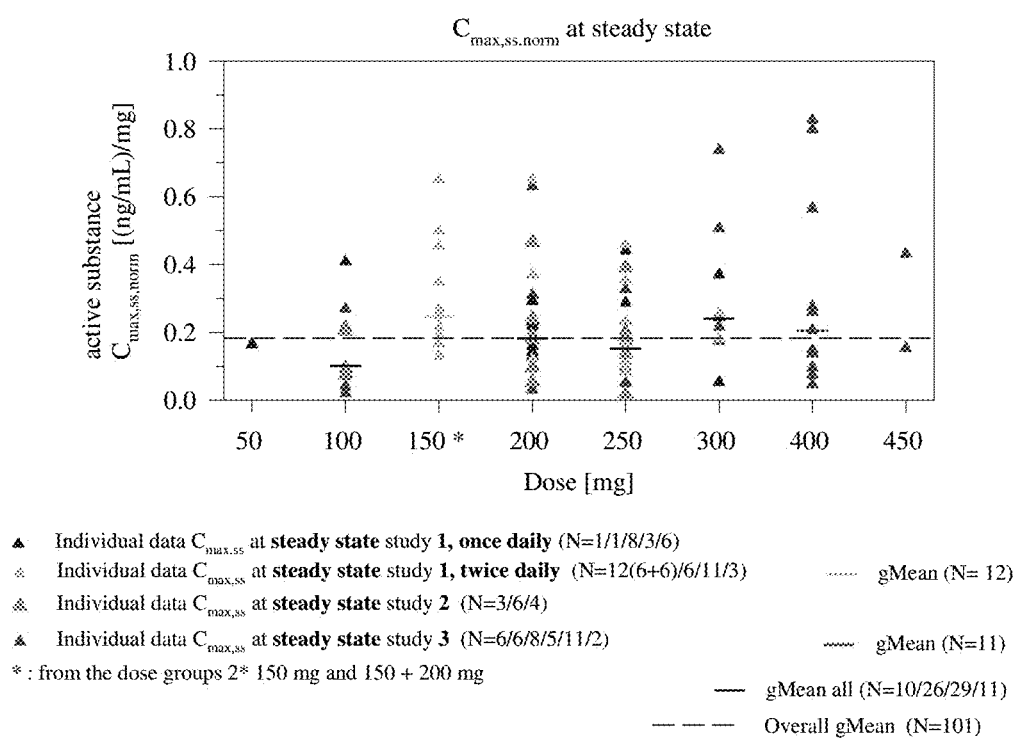

FIG. 9—Individual and geometric mean dose-normalized maximum plasma concentrations at steady state of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate from three different Phase I trials in cancer patients, after administration of the active substance in a soft gelatin capsule dosage form.

Figure 10:
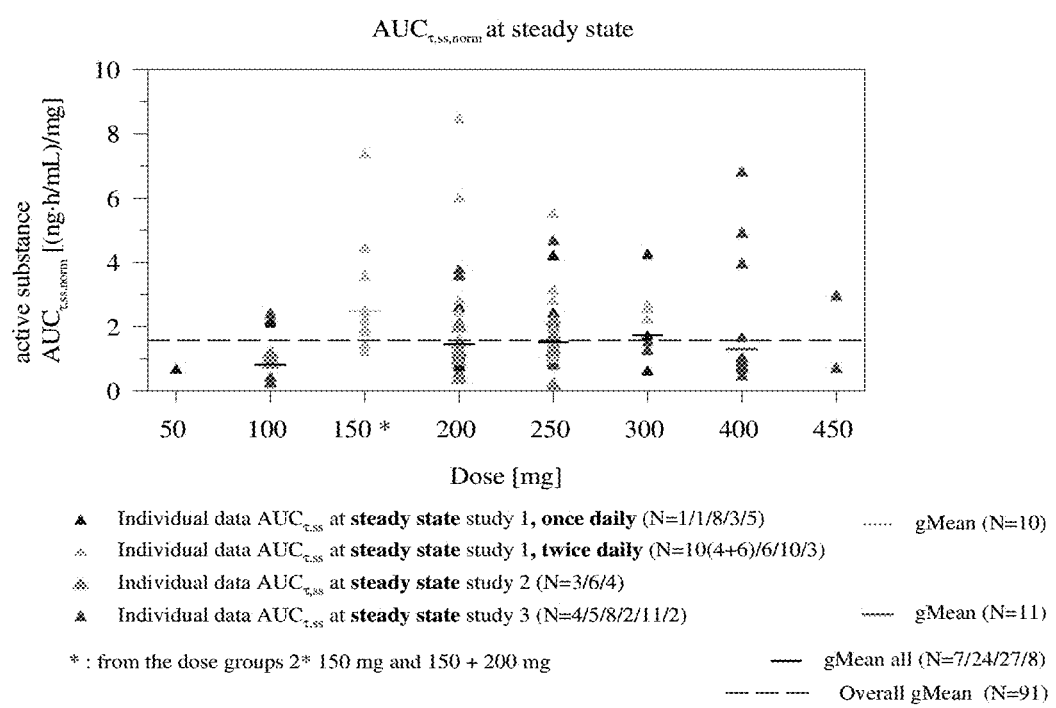

FIG. 10—Individual and geometric mean dose-normalized area under the curve (AUC) values at steady state of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate from three different Phase I trials in cancer patients, after administration of the active substance in a soft gelatin capsule dosage form.

DETAILED DESCRIPTION OF THE INVENTION

The methods for measuring the dissolution rate in accordance with the present invention are according to European Pharmacopeia 6.2 and described in the following.

The dissolution tests use Apparatus 2 (paddle) according to European Pharmacopeia 6.2, with a spindle rotation speed of 100 rpm and a dissolution medium without additives of 0.1 M HCl, pH 1.0, at 37° C. The method is adjustable to a change in the medium volume. Further methods include a stirring speed of between 50 and 150 rpm, using Apparatus 1 or 2 according to European Pharmacopeia 6.2, a dissolution medium with a pH of between 1 and 6.8, a volume of between 500 and 2000 ml, optionally using sinkers, optionally in the presence of surfactants and/or enzymes, and optionally in the presence of organic solvents or using common simulated intestinal or gastric fluids. In other conditions, such as when changing the pH of the dissolution medium, as shown in FIG. 6, the dissolution rate may be different. Hence, in accordance with the results of FIG. 6, the dissolution rate may decrease with an increase of the pH. This may be due to a change in the pH dependent solubility of the active substance. In addition, in the presence of surfactants the dissolution rate may increase. Further variations of the dissolution test conditions, such as temperature, rotation speed, volume or Apparatus may influence the dissolution rate as well.

In accordance with the present invention, dissolution tests with Apparatus 2 (paddle), 100 rpm, 900 mL pH 1.0 (0.1 M HCl) dissolution medium and 37° C., indicate that the lecithin amounts in the formulation are able to increase the dissolution rate, in contrast to the formulation without lecithin (FIG. 2).

Further, in accordance with the present invention, it can be shown that the dissolution behaviour of the drug product is independent of the dosage strength. FIG. 5 shows this for soft gelatin capsule dosage forms.

Furthermore, the dissolution profile comparison of soft gelatin capsules in the dissolution media pH 1.0 and pH 3.0 with and without surfactants indicates that the dissolution of formulations with this active substance may be improved in the presence of surfactants (FIG. 6).

In some instances, the measured dissolution rates with Apparatus 2 (paddle), 100 rpm, 900 mL pH 1.0 (0.1 M HCl) dissolution medium and 37° C., may show a significant difference in the dissolution behaviour of different batches of soft gelatin capsule pharmaceutical dosage forms. This is shown in FIG. 7, for two different batches used in a Phase I human bioavailability study (FIG. 8). As can be seen, for the measured values up to 60 minutes release time, batch A shows a faster release than batch B. However, this difference between the dissolution profile of different batches up to 60 minutes drug release observed with 100 rpm have no relevance on the in vivo pharmacokinetic behaviour of the active substance based on a immediate release formulation, as can be seen in FIG. 8.

In the Phase I study (see FIG. 9), the plasma concentrations of the active substance were measurable in a few subjects already 0.5 hours after drug administration and in most subjects one hour after drug administration. The plasma concentrations of the active substance increased up to about 2-4 hours after administration of the capsules to about 9 ng/mL (gMean value=geometric mean value) at a given dose of 150 mg to healthy subjects. Some subjects showed a second increase or a plateau in plasma concentrations of the active substance at about 4-6 hours. Afterwards the plasma concentration decreased in an at least bi-exponential manner The plasma concentrations of the active substance were about 15% of the maximum plasma concentration 24 hours after administration and about 7-8% 48 hours after administration. About ⅔ of the subjects had measurable plasma concentrations of the active substance 48 h after drug administration. The variability of the plasma concentrations of the active substance at the different time points was high up to 2 hours (gCV: 100-250%) but moderate at later time points (gCV: 30-45%).

So far, the plasma concentrations of the active substance displayed high inter-patient variability in PK parameters in all trials, which prevented a formal statistical testing of dose-proportionality. However, in three Phase I trials in cancer patients with various advanced solid tumors there was no sign for a deviation from a dose proportional increase in AUC and $C_{max}$ of the active substance observed through visual inspection neither after single dose nor at steady state for once and twice daily dosing (FIGS. 9 and 10). As a consequence, in cancer patients gMean $C_{max,ss}$ and $AUC_{\tau,ss}$ of the active substance increased in a dose-proportional manner after single dose and at steady state, for qd and bid dosing. There was no deviation from dose-proportionality observed for drug plasma concentrations measured before drug administration at steady state ($C_{pre,ss}$) in cancer patients in various clinical trials, found through visual inspection.

In addition, in two Phase 2 trials of monotherapy with the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate administered as soft gelatin capsule dosage form in patients with non small-cell lung cancer (NSCLC) or hormone refractory prostate cancer (HRPC), there was no obvious deviation from a dose proportional increase in pre-dose plasma concentrations of the active substance of both dose groups tested (150 and 250 mg twice daily of the active substance) at steady state.

Suitable preparations for the pharmaceutical dosage form in accordance with the present invention include for example tablets, capsules, or oral solutions, elixirs, emulsions, pellets, powders or granules. The proportion of the pharmaceutically active compound/active substance, i.e. 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate, should be in the range from 0.01 to 90 wt.-%, preferably 0.1 to 50 wt.-% of the composition as a whole, i.e. in amounts which are sufficient to achieve the dosage necessary to achieve a therapeutic effect. If necessary the doses specified may be given several times a day.

Suitable tablets may be obtained, for example, by mixing the active substance with known excipients, for example inert diluents such as calcium carbonate, calcium phosphate or lactose, disintegrants such as maize starch or alginic acid, binders such as starch or gelatin, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substance according to the invention, i.e. 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate, may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing the active substance in accordance with the present invention, i.e. 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate, may for example be prepared by mixing the active substance with inert carriers such as lactose or sorbitol and packing them into gelatin capsules.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may of course contain, apart from the abovementioned carriers, additives such as sodium citrate, calcium carbonate and dicalcium phosphate together with various additives such as starch, preferably potato starch, gelatin and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

The dosage for oral administration for humans is from 5-1000 mg per administration, preferably between 25 and 300 mg per administration, with one or more administrations per day.

However, it may sometimes be necessary to depart from the amounts specified, depending on the body weight, the route of administration, the individual response to the active substance, the nature of its formulation and the time or interval over which the active substance is administered. Thus, in some cases it may be sufficient to use less than the minimum dose given above, whereas in other cases the upper limit may have to be exceeded. When administering large amounts it may be advisable to divide them up into a number of smaller doses spread over the day.

The following further examples of pharmaceutical dosage forms illustrate the present invention without restricting its scope.

Active ingredients/substances or active moieties may be conveniently administered in liquid form either in a lipophilic or hydrophilic carrier system, either as a solution or a suspension, mixed with a single carrier excipient or mixed with a complex carrier medium made up of several components. Encapsulation of such liquid formulations in capsules, either soft (gelatin) or hard (gelatin-)capsules potentially offers a very convenient way of administering such pharmacologically active substances.

Solutions

To formulate a solution based system the carrier has to dissolve the active substance. Improved gastrointestinal (GI) absorption of poorly absorbable drugs can be achieved by increasing the dissolution rate of the drug in the presence of bile acids. Within the gastrointestinal tract, bile salts behave as biological detergents that, when mixed with phospholipids, form thermodynamically stable mixed micelles. In many instances the choice of formulation will be limited by solvent capacity, and in others the drug will not be sufficiently soluble in any lipid formulations.

The carrier medium may be designed to spontaneously form an emulsion or microemulsion in the stomach thereby facilitating absorption of the pharmacologically active substance. These systems are commonly known as self (micro-) emulsifying drug delivery systems (SEDDS or SMEDDS). They have to be accurately prepared and even slight variations in the composition cannot be tolerated without irreversibly upsetting the system, and destroying its beneficial properties. For example, the active substance may precipitate out as a consequence of a change in the solubilizing properties of the capsule formulation. This precipitation process may be irreversible and lead to an under-dosing of the patient. The emulsifying properties of the capsule formulation may also be changed, and, upon administration, an emulsion may not be formed in the stomach. As a consequence, the pharmacologically active substance may not be correctly or reproducibly absorbed.

Suspensions

As suspensions do represent thermodynamic instable multiphase systems, various characteristics have to be taken into account during development of these systems. The physical stability of the suspension formulation has to be ensured from the perspective of particle growth as well as from the perspective of re-crystallization in a potential polymorphic form which may have a different solubility or from the perspective of sedimentation associated by caking of the sediment. These factors may influence the liberation of the active substance from the dosage form and hence alter the extent of patient's exposure during the shelf-life of the product. Hence no solubility of the active substance in a single carrier excipient or in the carrier system would be the prerequisite for a physically stable system.

Lipophilic Carrier Systems

Lipophilic excipients are commonly employed as moisture barrier systems to protect chemically instable substances. For this purpose, different types of fats or waxes may be applied on solid dosage forms or on their manufacturing intermediates to prevent migration of ambient water vapour or oxygen and to improve the chemical stability of the active substance. Hot-melt inclusions of the drug into lipophilic binders may as well prevent contact with moisture. Since solid hydrophobic systems poorly disintegrate, drug release in these systems is delayed, in contrast to drug release in low viscous liquid lipid formulations. This delayed drug release is reflected by the specific plasma profiles of the active substance of a modified drug delivery system (Ritschel W. et al., Die Tablette, 2002, 2nd ed., ECV, Aulendorf, p. 2671). Hence, viscosity of liquid systems is a crucial parameter and has to be carefully adjusted to ensure adequate drug release.

In practice lipophilic or 'lipid' formulations are a diverse group of formulations which have a wide range of properties. These result from the blending of up to five classes of excipients, ranging from pure triglyceride oils, through mixed glycerides, lipophilic surfactants, hydrophilic surfactants and water-soluble cosolvents.

Assessment of Quality

The performance of a formulation may be assessed by measuring its relative bioavailability, i.e. comparing its bioavailability with the bioavailability of an aqueous solution of the active substance. Thus, (lipid) suspensions may also show satisfactory exposure of the patient due to the adequate solubility of the active substance within physiological conditions.

In other respects, if an increase of the drug release of the drug product in the presence of surfactants is observed, it can be expected that the drug release of the drug product is improved as well under in vivo conditions when tensides out of the gastrointestinal tract are present.

A soft gelatin capsule including a liquid formulation comprising a viscous suspension of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate in medium chain triglycerides, hard fat and lecithin, meets the adequate bioavailability requirements for the desired dosage range tailored to treatment with the drug substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate. This liquid formulation consists of a lipid suspension of the active substance. This formulation further meets the specific immediate release profile range providing an appropriate plasma concentration-time profile of the active principle which is the aim of the present invention.

An advantage of such soft gelatin capsule containing a lipid suspension is that the water uptake into the formulation is very unlikely. The dosage form is divided into three different compartments, namely (a) a hydrophilic capsule shell and (b) the hydrophobic carrier system in which (c) the slightly hygroscopic powder of active substance is suspended. Due to ambient moisture the content of water may vary within these different compartments. It will migrate by diffusion until an equilibrium state is reached. The water content may affect different properties of the drug product, such as the chemical stability of the active substance (predominantly via hydrolysis), the dissolution of the active substance, or the elasticity of the capsule shell. The water uptake in the present system is primarily in the capsule shell. This can be shown by water vapour sorption experiments as well as by the correlation of the mass gain with the softening of the capsule (shown in FIG. 1). The water uptake does further not affect the chemical stability of the drug substance. This is confirmed by the stress stability studies of, for example, 1 month at 70° C., and by long-term (3 years) and accelerated (6 months) stability study results for the systems in accordance with the present invention.

Furthermore, studies have shown that there is no relevant mass increase or sticking problem for the capsules in accordance with the present invention when stored in tight packaging materials below 30° C. Thus, recommended packaging for such capsules are, for example, glass containers or flexible/hard plastic containers (e.g. HDPE bottles), aluminium blisters (e.g. alu/alu blisters), plastic blisters (e.g. PVC, PVDC or Aclar®) optionally with an over-packaging of an aluminium pouch, or an aluminium pouch or double poly bag.

Generally, soft gelatin capsules have a capsule shell made of gelatin, one or more plasticizing agents, in particular glycerol, optionally further auxiliary materials, such as dyes, colorant pigments, flavouring agents, sugar, oligosaccharides or polysaccharides, and a capsule formulation (or capsule filling) containing a solvent, adjuvants and one or more pharmacologically active substances. The term gelatin as used herein includes not only unmodified gelatin as in the European Pharmacopeia but also modified gelatin, such as for example succinated gelatin.

The above-mentioned lipid suspension formulation of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate comprises a viscous suspension of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate in a lipid carrier, a thickener and a glidant/solubilizing agent.

The amount of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate is preferably comprised within the range of 1 to 90 weight % of the lipid suspension formulation, most preferably within 10 and 50%.

To avoid the above-mentioned physical stability issues, such as re-crystallization or particle-growth, the active substance must be either completely insoluble or dissolved in the carrier. A solubility screening of lipophilic hydrophilic and amphiphilic excipients and mixtures revealed various potential carriers for formulating the above-mentioned lipid suspension.

Thus, suitable carriers or carrier components for the active substance 3-Z-[1-4-(N-((4-methyl-piperazin-1-yl)-methylcarbonyl)-N-methyl-amino)-anilino)-1-phenyl-methylene]-6-methoxycarbonyl-2-indolinone-monoethanesulphonate are acetylated monoglycerides, corn oil glycerides, ethyl oleate, glycerol mono/dioleate, glycerol monolinolate, macrogolglycerol caprylocaprate, macrogolglycerol linoleate, medium chain partial glycerides, medium chain triglycerides, caprylic-capric triglycerides, caprylic/capric/linoleic triglycerides, caprylic/capric/succinic triglycerides, propylene glycol dicaprylate/dicaprate, oleic acid polyoxyl castor oil, polyoxyl hydrogenated castor oil, propylene glycol monocaprylate, propylene glycol monolaurate, refined animal derived oil, refined soybean oil, refined vegetable oil, sorbitan monostearate, triacetin, triethyl citrate, or mixtures thereof.

Stability issues such as hydrolytic degradation of the active substance may also be caused by hydrophilic carrier components. Therefore, carrier systems based on hydrophilic polyethylene glycols will generally show inferior stability than more hydrophobic carriers such as lipid carriers.

In the above-mentioned lipid suspension formulation, the most preferred lipid carrier is medium chain triglycerides. It is comprised within the range of 1 to 90 weight % of the lipid suspension formulation, preferably within 10 and 70%. Suitable medium chain triglycerides may be the commercial product Miglyol 812®, Miglyol 810®, Miglyol 818®, Miglyol 829® or Miglyol 840®.

A thickener adjusts the viscosity of the suspension. It stabilizes the suspension system, ensures optimal processing and guarantees an adequate capsule quality, especially as far as content uniformity or dissolution behaviour are concerned. Suitable thickeners to be used for the above-mentioned suspension formulation are oleogel forming excipients, such as Colloidal Silica or Bentonit, or lipophilic or amphiphilic excipients of high viscosity, such as bees wax, glycerol monostearate, hydrogenated vegetable oil, partially hydrogenated vegetable oil or hard fats.

In the above-mentioned suspension formulation, the most preferred thickener is hard fat. It is preferably comprised within the range of 1 to 30 weight % of the suspension formulation, most preferably within 10 and 30 weight %. The most suitable hard fats have a melting range of 30° C. to 44° C., most preferably a melting range of 33° C. to 40° C. Suitable commercially available products are Gelucire® 33/01, Witepsol ®W35 or Softisan® 378. The determination of the most suitable melting range for hard fats can be performed as shown in FIG. 3, by measurement of the effect of the melting range of the hard fat on the in-vitro dissolution behaviour over time.

Lecithin is a common excipient for carrier-systems in soft gelatin capsules. It is used as a glidant of the highly concentrated suspension during encapsulation, prevents blocking of ducts and pumps and ensures high mass uniformity of the encapsulated formulation. Furthermore Lecithin acts as a surfactant, which may improve distribution of the formulation-droplets during in-vitro dissolution testing (compare FIG. 2) as well as in-vivo for drug resorption. Furthermore it may also improve wetting of the active substance crystals. Suitable lecithin may be the commercial product Topcithin®.

Lecithin, up to a certain content, is useful to improve the dissolution behaviour of the finished capsules. Exceeding amounts do not show an additional benefit during in-vitro dissolution testing, as shown in FIG. 2.

In the above-mentioned lipid suspension formulation, the amount of lecithin is comprised within the range of 0.1 to 10 weight % of the lipid suspension formulation, most preferably within 0.25 and 2.5%.

Alternatively, the lipid suspension formulation of the active substance 3-Z-[1-4-(N-((4-methyl-piperazin-1-yl)-methylcarbonyl)-N-methyl-amino)-anilino)-1-phenyl-methylene]-6-methoxycarbonyl-2-indolinone-monoethanesulphonate comprises a viscous suspension of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate in medium chain triglycerides, hard fat, lecithin and one or more macrogolglycerols, such as for example macrogolglycerol-hydroxystearate (traded for example under the name Eumulgin® HRE 40 PH) or macrogolglycerol-ricinoleate (also known as polyoxyl castor oil and traded for example under the name Cremophor® EL, Cremophor® RH40 or Eumulgin® RO 35 PH).

In the above-mentioned lipid suspension formulation, the amount of macrogolglycerol(s) is comprised within the range of 0.1 to 50 weight % of the lipid suspension formulation, most preferably within 0.3 and 10%.

Three carrier systems (the hydrophilic P3, lipophilic P1 and lipophilic with surfactants P2 semi-solid suspension formulations described in the foregoing) were tested for bioavailability in non-clinical studies and all of them were identified to be suitable options for an oral dosage form of the active substance 3-Z-[1-4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

However, for reasons of bioavailability, as is evident from the results shown in FIG. 4, lipid (lipophilic) suspension formulations comprising a viscous suspension of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate in medium chain triglycerides, hard fat and lecithin are preferred.

Hence, FIG. 4 shows the results of a comparison of the absolute bioavailability (BA in %) tested in the rat over 24 hours for the aqueous solution (S) versus different carrier systems (P1, P2 and P3) of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate. The experiment is described in the following.

The table below shows the composition of the tested carrier systems (semi-solid suspension formulations).

| Formulation Ingredients | P1 | P2 [%]* | P3 |
|---|---|---|---|
| Active Substance | 43.48 | 42.19 | 31.75 |
| Triglycerides, Medium-Chain | 37.83 | 41.77 | — |
| Hard fat | 18.26 | 12.66 | — |
| Cremophor RH40 | — | 2.95 | — |
| Lecithin | 0.43 | 0.42 | — |
| Glycerol 85% | — | — | 3.17 |
| Purified Water | — | — | 4.76 |
| Macrogol 600 | — | — | 58.10 |
| Macrogol 4000 | — | — | 2.22 |

*slight deviations of the quantities towards 100 percent may be caused by rounding errors The semi-solid suspensions are filled in hard gelatin capsules (Capsugel, no. Y0303490). Each capsule contains approximately 15 to 20 mg of the formulation. The capsules are applied to the rats with a special device similar to gavage. For comparison an aqueous solution containing 0.5% Natrosol 250 HX is applied via gavage. For calculation of the absolute bioavailability an additional group of rats is dosed intravenously with the compound dissolved in 5% glucose solution (aqueous solution (S)). 5 male Han Wistar rats (strain: CrlGlxBrlHan:WI) are used per group. Blood sampling times were 0.5 h, 1 h, 2 h, 4 h, 8 h, 24 h post dose and plasma was analysed by a validated HPLC/MS/MS method. From the plasma level time curves areas under the curve (AUC) were calculated by linear trapezoidal rule. Dose normalised AUCs of the oral formulation are divided by dose normalised AUCs of the intravenous formulation for the calculation of the absolute bioavailability. As can be seen from the results of the experiment shown in FIG. 4, the bioavailability is similar for the aqueous solution (S: 11%) and the different carrier systems of active substance (P1: 14%, P2: 10% and P3: 10%), however the inter-individual variation (standard deviation of bioavailability) is smaller for the aqueous solution (S) and the carrier system (P1) when compared to the carrier systems (P2) and (P3) (2.8 and 4.1 versus 7.4 and 7.1), indicating a practically complete relative bioavailability for the tested formulations (P1, P2 and P3) versus the solution (S) but a higher variation in the carrier systems (P2) and (P3).

The lipid suspension formulation as hereinbefore described may be part of a capsule pharmaceutical dosage form consisting of a capsule shell and a capsule formulation (or capsule filling), in which the capsule formulation (or capsule filling) comprises the lipid suspension formulation as hereinbefore described. The capsule pharmaceutical dosage form may be a soft gelatin capsule, a hard gelatin capsule, or an hydroxypropylmethylcellulose (HPMC) capsule, a polyvinyl alcohol polymer capsule or a pullulan capsule.

In the case of a hard gelatin capsule or an hydroxypropylmethylcellulose (HPMC) capsule, a polyvinyl alcohol polymer capsule or a pullulan capsule, the filled in capsule may further be sealed or banded.

Preferably, the capsule is a soft gelatin capsule consisting of a capsule shell comprising gelatin, one or more plasticizing agents and optionally further auxiliary materials, and a capsule formulation (or capsule filling), characterized in that the capsule formulation (or capsule filling) comprises the lipid suspension formulation as hereinbefore described.

The capsule pharmaceutical dosage form, and especially the soft gelatin capsules, may be stored in suitable glass containers or in flexible/hard plastic containers, preferably non-PVC materials based, or in plastic (e.g. PVC, PVDC or Aclar®) blisters optionally with an over-packaging of aluminium (aluminium pouch), or in aluminium blisters consisting of e.g a bottom foil of PA/Al/PVC and an aluminium lidding foil, the later providing the highest water protection. Hence, the containers may be designed so as to provide particular protection for the capsule pharmaceutical dosage form, and especially the soft gelatin capsules, e.g. to protect them from light, oxygen or water. Flexible plastic containers may contain additional protection, e.g. in the form of an additional aluminium packaging.

The capsule pharmaceutical dosage form may be prepared by conventional methods of producing capsules known from the literature. The soft gelatin capsule may be prepared by conventional methods of producing soft gelatin capsules known from the literature, such as for example the "rotary die procedure", described for example in Swarbrick, Boylann, Encyclopedia of pharmaceutical technology, Marcel Dekker, 1990, Vol. 2, pp 269 ff or in Lachmann et al., "The Theory and Practice of Industrial Pharmacy", 2nd Edition, pages 404-419, 1976, or other procedures, such as those described for example in Emerson R. F. et al., "Soft gelatin capsule update", Drug Dev. Ind. Pharm., Vol. 12, No. 8-9, pp. 1133-44, 1986.

The lipid suspension formulation may be prepared by conventional methods of producing formulations known from the literature, i.e. by mixing the ingredients at a pre-determined temperature in a pre-determined order in order to obtain a homogenized suspension.

Alternatively, the lipid suspension formulation may be prepared in accordance with the procedure described in Example 10.

Lipid suspension formulation of the active substance, finished soft gelatin capsules containing same and packaging materials for the packaging of finished soft gelatin capsules are illustrated by the Examples and Figures that follow. The Examples serve purely as an illustration and are not to be construed in a limiting capacity.

Examples of carrier systems (formulations), soft gelatin capsules, packaging materials, and of a manufacturing process for the preparation of a lipid suspension formulation of the active substance The active substance in all the Examples is 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

EXAMPLE 1

Lipid Based Carrier System

| Formulation Ingredients | A | B [%]* | C |
|---|---|---|---|
| Active Substance | 43.48 | 43.48 | 43.48 |
| Triglycerides, Medium-Chain | 28.70 | 37.83 | 38.045 |
| Hard fat | 27.39 | 18.26 | 18.26 |
| Lecithin | 0.43 | 0.43 | 0.215 |

*slight deviations of the quantities towards 100 percent may be caused by rounding errors

EXAMPLE 2

Lipid Based Carrier System with Additional Surfactant

| Ingredients | [%]* |
|---|---|
| Active Substance | 42.19 |
| Triglycerides, Medium-Chain | 41.77 |
| Hard fat | 12.66 |
| Cremophor RH40 | 2.95 |
| Lecithin | 0.42 |

*slight deviations of the quantities towards 100 percent may be caused by rounding errors

EXAMPLE 3

Hydrophilic Carrier System

| Ingredients | [%]* |
|---|---|
| Active Substance | 31.75 |
| Glycerol 85% | 3.17 |
| Purified Water | 4.76 |
| Macrogol 600 | 58.10 |
| Macrogol 4000 | 2.22 |

*slight deviations of the quantities towards 100 percent may be caused by rounding errors

EXAMPLE 4

Soft Gelatin Capsule Containing 50 mg of Active Substance

| Ingredients | Function | Formulation A mg per capsule | Formulation B mg per capsule | Formulation C mg per capsule |
|---|---|---|---|---|
| Active Substance* | Active Ingredient | 60.20 | 60.20 | 60.20 |
| Triglycerides, Medium-chain | Carrier | 40.95 | 53.70 | 54.00 |
| Hard fat | Thickener | 38.25 | 25.50 | 25.50 |
| Lecithin | Wetting agent/Glidant | 0.60 | 0.60 | 0.30 |
| Gelatin | Film-former | 72.25 | 72.25 | 72.25 |
| Glycerol 85% | Plasticizer | 32.24 | 32.24 | 32.24 |
| Titanium dioxide | Colorant | 0.20 | 0.20 | 0.20 |
| Iron oxide A | Colorant | 0.32 | 0.32 | 0.32 |
| Iron oxide B | Colorant | 0.32 | 0.32 | 0.32 |
| Total Capsule Weight | | 245.33 | 245.33 | 245.33 |

*The figures refer to the amount of ethanesulfonate salt (dry basis) equivalent to the labeled amount of the free base EXAMPLE 4a Soft Gelatin Capsule Containing 75 mg of Active Substance

| Ingredients | Function | Formulation A mg per capsule | Formulation B mg per capsule | Formulation C mg per capsule |
|---|---|---|---|---|
| Active Substance* | Active Ingredient | 90.3 | 90.3 | 90.3 |
| Triglycerides, Medium-chain | Carrier | 61.425 | 80.55 | 80.1 |
| Hard fat | Thickener | 57.375 | 38.25 | 38.25 |
| Lecithin | Wetting agent/Glidant | 0.9 | 0.9 | 1.35 |
| Gelatin | Film-former | 107.11 | 107.11 | 107.11 |
| Glycerol 85% | Plasticizer | 46.84 | 46.84 | 46.84 |
| Titanium dioxide | Colorant | 0.35 | 0.35 | 0.35 |

| Ingredients | Function | Formulation A mg per capsule | Formulation B mg per capsule | Formulation C mg per capsule |
|---|---|---|---|---|
| Iron oxide A | Colorant | 0.058 | 0.058 | 0.058 |
| Iron oxide B | Colorant | 0.16 | 0.16 | 0.16 |
| Total Capsule Weight | | 364.518 | 364.518 | 364.518 |

*The figures refer to the amount of ethanesulfonate salt (dry basis) equivalent to the labeled amount of the free base

EXAMPLE 5

Soft Gelatin Capsule Containing 100 mg of Active Substance

| Ingredients | Function | Formulation A mg per capsule | Formulation B mg per capsule | Formulation C mg per capsule |
|---|---|---|---|---|
| Active Substance* | Active Ingredient | 120.40 | 120.40 | 120.40 |
| Triglycerides, Medium-chain | Carrier | 81.90 | 107.40 | 106.8 |
| Hard fat | Thickener | 76.50 | 51.00 | 51.00 |
| Lecithin | Wetting agent/ Glidant | 1.20 | 1.20 | 1.80 |
| Gelatin | Film-former | 111.58 | 111.58 | 111.58 |
| Glycerol 85% | Plasticizer | 48.79 | 48.79 | 48.79 |
| Titanium dioxide | Colorant | 0.36 | 0.36 | 0.36 |
| Iron oxide A | Colorant | 0.06 | 0.06 | 0.06 |
| Iron oxide B | Colorant | 0.17 | 0.17 | 0.17 |
| Total Capsule Weight | | 440.96 | 440.96 | 440.96 |

*The figures refer to the amount of ethanesulfonate salt (dry basis) equivalent to the labeled amount of the free base

EXAMPLE 6

Soft Gelatin Capsule Containing 125 mg of Active Substance

| Ingredients | Function | Formulation A mg per capsule | Formulation B mg per capsule | Formulation C mg per capsule |
|---|---|---|---|---|
| Active Substance* | Active Ingredient | 150.50 | 150.50 | 150.50 |
| Triglycerides, Medium-chain | Carrier | 102.375 | 134.25 | 133.5 |
| Hard fat | Thickener | 95.625 | 63.75 | 63.75 |
| Lecithin | Wetting agent/ Glidant | 1.50 | 1.50 | 2.25 |
| Gelatin | Film-former | 142.82 | 142.82 | 142.82 |
| Glycerol 85% | Plasticizer | 62.45 | 62.45 | 62.45 |

| Ingredients | Function | Formulation A mg per capsule | Formulation B mg per capsule | Formulation C mg per capsule |
|---|---|---|---|---|
| Titanium dioxide | Colorant | 0.47 | 0.47 | 0.47 |
| Iron oxide A | Colorant | 0.08 | 0.08 | 0.08 |
| Iron oxide B | Colorant | 0.22 | 0.22 | 0.22 |
| Total Capsule Weight | | 556.04 | 556.04 | 556.04 |

*The figures refer to the amount of ethanesulfonate salt (dry basis) equivalent to the labeled amount of the free base

EXAMPLE 7

Soft Gelatin Capsule Containing 150 mg of Active Substance

| Ingredients | Function | Formulation A mg per capsule | Formulation B mg per capsule | Formulation C mg per capsule |
|---|---|---|---|---|
| Active Substance* | Active Ingredient | 180.60 | 180.60 | 180.60 |
| Triglycerides, Medium-chain | Carrier | 122.85 | 161.10 | 160.20 |
| Hard fat | Thickener | 114.75 | 76.50 | 76.50 |
| Lecithin | Wetting agent/ Glidant | 1.80 | 1.80 | 2.70 |
| Gelatin | Film-former | 142.82 | 142.82 | 142.82 |
| Glycerol 85% | Plasticizer | 62.45 | 62.45 | 62.45 |
| Titanium dioxide | Colorant | 0.47 | 0.47 | 0.47 |
| Iron oxide A | Colorant | 0.08 | 0.08 | 0.08 |
| Iron oxide B | Colorant | 0.22 | 0.22 | 0.22 |
| Total Capsule Weight | | 626.04 | 626.04 | 626.04 |

*The figures refer to the amount of ethanesulfonate salt (dry basis) equivalent to the labeled amount of the free base

EXAMPLE 8

Soft Gelatin Capsule Containing 200 mg of Active Substance

| Ingredients | Function | Formulation A mg per capsule | Formulation B mg per capsule | Formulation C mg per capsule |
|---|---|---|---|---|
| Active Substance* | Active Ingredient | 240.80 | 240.80 | 240.80 |
| Triglycerides, Medium-chain | Carrier | 163.30 | 214.80 | 216.00 |
| Hard fat | Thickener | 153.50 | 102.00 | 102.00 |
| Lecithin | Wetting agent/ Glidant | 2.40 | 2.40 | 1.20 |
| Gelatin | Film-former | 203.19 | 203.19 | 203.19 |
| Glycerol 85% | Plasticizer | 102.61 | 102.61 | 102.61 |
| Titanium dioxide | Colorant | 0.57 | 0.57 | 0.57 |

-continued

| Ingredients | Function | Formulation A mg per capsule | Formulation B mg per capsule | Formulation C mg per capsule |
|---|---|---|---|---|
| Iron oxide A | Colorant | 0.90 | 0.90 | 0.90 |
| Iron oxide B | Colorant | 0.90 | 0.90 | 0.90 |
| Total Capsule Weight | | 868.17 | 868.17 | 868.17 |

*The figures refer to the amount of ethanesulfonate salt (dry basis) equivalent to the labeled amount of the free base

EXAMPLE 9

Packaging materials for the packaging of the soft gelatin capsules of above examples 4 to 8 may be glass containers, flexible/hard plastic containers or PVC/PVDC blisters, optionally within an aluminium pouch, or alu/alu blisters.

EXAMPLE 10

In the following, a manufacturing process for the preparation of a lipid suspension formulation of the active substance and a process for the encapsulation are described.

a: Hard fat and parts of Medium-chain triglycerides are pre-mixed in the processing unit. Subsequently lecithin, the rest of medium-chain triglycerides and the active substance are added. The suspension is mixed, homogenized, de-aerated and finally sieved to produce the formulation (Fillmix)

b. The gelatin basic mass components (glycerol, water and gelatin) are mixed and dissolved at elevated temperature. Then, the corresponding colours are added and mixed, producing the Coloured Gelatin Mass.

c. After adjustment of the encapsulation machine, Fillmix and Coloured Gelatin Mass are processed into soft gelatin capsules using the rotary-die process. This process is e.g. described in Swarbrick, Boylann, Encyclopedia of pharmaceutical technology, Marcel Dekker, 1990, Vol. 2, pp 269 ff.

d. The initial drying is carried out using a rotary dryer. For the final drying step, capsules are placed on trays. Drying is performed at 15-26° C. and low relative humidity.

e. After 100% visual inspection of the capsules for separation of deformed or leaking capsules, the capsules are size sorted.

f. Finally, the capsules are imprinted, using an Offset printing technology or an Ink-jet printing technology. Alternatively, the capsule imprint can be made using the Ribbon printing technology, a technology in which the gelatin bands are imprinted prior to the encapsulation step c.

EXAMPLE 11

The table below shows alternative pharmaceutical compositions according to the invention. D, E and F are tablets, G can be compressed to form tablets after hot melt-granulation of the active substance in a heated/cooled high-shear mixer together with Microcrystalline cellulose an Macrogol 6000. After further mixing steps of the obtained granules with the other excipients, tablets are produced on a conventional tablet press. Alternatively it can be directly dispensed as oral granules into sachets.

Tablet D and F may be produced by direct blending of the components and subsequent compression on a conventional tablet press. Alternatively it can be extruded to pellets and filled into a hard capsule.

Tablet E may be produced by wet granulation of the drug substance together with Lactose monohydrate and Microcrystalline cellulose by an aqueous solution of Copovidone. After further blending steps with Crospovidone, Colloidal silica and Magnesium stearate, the tablets are compressed on a conventional tablet press.

EXEMPLARY COMPOSITION OF FURTHER SOLID ORAL FORMULATIONS

| Formulation | D | E | F | G | H | I |
|---|---|---|---|---|---|---|
| Active Substance | 180.6 mg | 150.5 mg | 120.4 mg | 150.5 mg | 60.2 mg | 60.2 mg |
| Sorbitol | — | — | — | — | — | 125.0 mg |
| Lactose monohydrate | 50.0 mg | 125.0 mg | — | — | — | — |
| Microcrystalline cellulose | — | 20.0 mg | 150.0 mg | 80.0 mg | — | 20.0 mg |
| Calcium phopsphate | 30.0 mg | — | 150.0 mg | — | — | — |
| Soybean Oil | — | — | — | — | 145.0 mg | — |
| Macrogol 6000 | — | — | — | 80.0 mg | — | — |
| Copovidone | 2.0 mg | 10.0 mg | — | — | — | — |
| Sodium starch glycolate | 5.0 mg | — | — | — | — | — |
| Crospovidone | — | 5.0 mg | 5.0 mg | — | — | 5.0 mg |
| Cremophor RH 40 | — | — | — | — | 20.0 mg | — |
| Colloidal silica | 1.0 mg | 1.0 mg | 1.0 mg | — | 10.0 mg | 1.0 mg |
| Solid flavour | — | — | — | 5.0 mg | — | 4.0 mg |
| Magnesium stearate | 4.0 mg | 4.0 mg | 4.0 mg | — | — | — |
| Total | 272.6 mg | 315.5 mg | 430.4 mg | 315.5 mg | 235.2 mg | 215.2 mg |

Formulation H is prepared as a liquid fillmix of suspended active. After homogenization it is filled either in hard or soft gelatin capsules. Formulation I is an oral powder.

The invention claimed is:

1. A pharmaceutical dosage form which is a viscous lipid suspension formulation comprising:
   10 to 50 wt. % of the active substance 3-Z-[1-(4-(N-((4-methyl-piperazin-1-yl)-methylcarbonyl)-N-methyl-amino)-anilino)-1-phenyl-methylenel]-6-methoxycarbonyl-2-indolinone-monoethanesulphonate,
   10 to 70 wt. % of medium chain triglycerides;
   10 to 30 wt. % of hard fat; and
   0.25 to 2.5 wt. % of lecithin, which delivers an immediate release profile in which not less than 70% (Q65%) of the active substance is dissolved in 60 minutes in vitro under the following in vitro dissolution conditions according to European Pharmacopeia 6.2: Apparatus 2 (paddle), dissolution medium with 0.1 M HCl (pH 1) and stirring speed of 50 to 150 rpm, at a temperature of 37° C.

2. The pharmaceutical dosage form according to claim 1, wherein it is an orally deliverable dosage form.

3. The pharmaceutical dosage form according to claim 2, wherein it is in the form of a capsule.

4. The pharmaceutical dosage form according to claim 3 in the form of a soft gelatine capsule comprising 50 mg of active substance free base equivalent selected from the group consisting of compositions A, B and C:

| Ingredients | Formulation A mg per capsule | Formulation B mg per capsule | Formulation C mg per capsule |
|---|---|---|---|
| Active Substance* | 60.20 | 60.20 | 60.20 |
| Triglycerides, Medium-chain | 40.95 | 53.70 | 54.00 |
| Hard fat | 38.25 | 25.50 | 25.50 |
| Lecithin | 0.60 | 0.60 | 0.30 |
| Gelatin | 72.25 | 72.25 | 72.25 |
| Glycerol 85% | 32.24 | 32.24 | 32.24 |
| Titanium dioxide | 0.20 | 0.20 | 0.20 |
| Iron oxide A | 0.32 | 0.32 | 0.32 |
| Iron oxide B | 0.32 | 0.32 | 0.32 |
| Total Capsule Weight | 245.33 | 245.33 | 245.33. |

5. The pharmaceutical dosage form according to claim 3 in the form of a soft gelatine capsule comprising 75 mg of active substance free base equivalent selected from the group consisting of A, B and C:

| Ingredients | Formulation A mg per capsule | Formulation B mg per capsule | Formulation C mg per capsule |
|---|---|---|---|
| Active Substance* | 90.3 | 90.3 | 90.3 |
| Triglycerides, Medium-chain | 61.425 | 80.55 | 80.1 |
| Hard fat | 57.375 | 38.25 | 38.25 |
| Lecithin | 0.9 | 0.9 | 1.35 |
| Gelatin | 107.11 | 107.11 | 107.11 |
| Glycerol 85% | 46.84 | 46.84 | 46.84 |
| Titanium dioxide | 0.35 | 0.35 | 0.35 |
| Iron oxide A | 0.058 | 0.058 | 0.058 |
| Iron oxide B | 0.16 | 0.16 | 0.16 |
| Total Capsule Weight | 364.518 | 364.518 | 364.518. |

6. The pharmaceutical dosage form according to claim 3 in the form of a soft gelatine capsule comprising 100 mg of active substance free base equivalent selected from the group consisting of compositions A, B and C:

| Ingredients | Formulation A mg per capsule | Formulation B mg per capsule | Formulation C mg per capsule |
|---|---|---|---|
| Active Substance* | 120.40 | 120.40 | 120.40 |
| Triglycerides, Medium-chain | 81.90 | 107.40 | 106.8 |
| Hard fat | 76.50 | 51.00 | 51.00 |
| Lecithin | 1.20 | 1.20 | 1.80 |
| Gelatin | 111.58 | 111.58 | 111.58 |
| Glycerol 85% | 48.79 | 48.79 | 48.79 |
| Titanium dioxide | 0.36 | 0.36 | 0.36 |
| Iron oxide A | 0.06 | 0.06 | 0.06 |
| Iron oxide B | 0.17 | 0.17 | 0.17 |
| Total Capsule Weight | 440.96 | 440.96 | 440.96. |

7. The pharmaceutical dosage form according to claim 3 in form of a soft gelatine capsule comprising 125 mg of active substance free base equivalent, selected from the group consisting of compositions A, B and C:

| Ingredients | Formulation A mg per capsule | Formulation B mg per capsule | Formulation C mg per capsule |
|---|---|---|---|
| Active Substance* | 150.50 | 150.50 | 150.50 |
| Triglycerides, Medium-chain | 102.375 | 134.25 | 133.5 |
| Hard fat | 95.625 | 63.75 | 63.75 |
| Lecithin | 1.50 | 1.50 | 2.25 |
| Gelatin | 142.82 | 142.82 | 142.82 |
| Glycerol 85% | 62.45 | 62.45 | 62.45 |
| Titanium dioxide | 0.47 | 0.47 | 0.47 |
| Iron oxide A | 0.08 | 0.08 | 0.08 |
| Iron oxide B | 0.22 | 0.22 | 0.22 |
| Total Capsule Weight | 556.04 | 556.04 | 556.04. |

8. The pharmaceutical dosage form according to claim 3 in form of a soft gelatine capsule comprising 150 mg of active substance free base equivalent selected from the group consisting of compositions A, B and C:

| Ingredients | Formulation A mg per capsule | Formulation B mg per capsule | Formulation C mg per capsule |
|---|---|---|---|
| Active Substance* | 180.60 | 180.60 | 180.60 |
| Triglycerides, Medium-chain | 122.85 | 161.10 | 160.20 |
| Hard fat | 114.75 | 76.50 | 76.50 |
| Lecithin | 1.80 | 1.80 | 2.70 |
| Gelatin | 142.82 | 142.82 | 142.82 |
| Glycerol 85% | 62.45 | 62.45 | 62.45 |
| Titanium dioxide | 0.47 | 0.47 | 0.47 |
| Iron oxide A | 0.08 | 0.08 | 0.08 |
| Iron oxide B | 0.22 | 0.22 | 0.22 |
| Total Capsule Weight | 626.04 | 626.04 | 626.04. |

9. The pharmaceutical dosage form according to claim 3 in a soft gelatine capsule comprising 200 mg of active substance free base equivalent selected from the group consisting of compositions A, B and C:

| Ingredients | Formulation A mg per capsule | Formulation B mg per capsule | Formulation C mg per capsule |
|---|---|---|---|
| Active Substance* | 240.80 | 240.80 | 240.80 |
| Triglycerides, Medium-chain | 163.30 | 214.80 | 216.00 |
| Hard fat | 153.50 | 102.00 | 102.00 |
| Lecithin | 2.40 | 2.40 | 1.20 |
| Gelatin | 203.19 | 203.19 | 203.19 |
| Glycerol 85% | 102.61 | 102.61 | 102.61 |
| Titanium dioxide | 0.57 | 0.57 | 0.57 |
| Iron oxide A | 0.90 | 0.90 | 0.90 |
| Iron oxide B | 0.90 | 0.90 | 0.90 |
| Total Capsule Weight | 868.17 | 868.17 | 868.17. |

10. The pharmaceutical dosage form according to claim 1, comprising dose-range values of between 25 to 300 mg of the active substance.

* * * * *